(12) United States Patent
Erickson (10) Patent No.: US 6,592,769 B1
(45) Date of Patent: *Jul. 15, 2003

(54) FILTER AND COLLECTION DEVICE FOR SEPARATING MATERIALS AND USE THEREOF

(76) Inventor: Roger T. Erickson, 1010 Broncho Rd., Pebble Beach, CA (US) 93953

( * ) Notice: Subject to any disclaimer, the term of this patent is extended or adjusted under 35 U.S.C. 154(b) by 0 days.

This patent is subject to a terminal disclaimer.

(21) Appl. No.: 09/642,235

(22) Filed: Aug. 17, 2000

Related U.S. Application Data (63) Continuation-in-part of application No. 09/176,812, filed on Oct. 22, 1998, now Pat. No. 6,149,812.

(51) Int. Cl.$^7$ .......................... A61C 17/06; B01D 21/00
(52) U.S. Cl. .......................... 210/801; 210/86; 210/94; 210/521; 210/532.1; 433/92; 433/97
(58) Field of Search .................. 210/254, 513, 210/521, 532.1, 94, 86, 800, 801; 433/92, 97

(56) References Cited

U.S. PATENT DOCUMENTS

| | | | | | |
|---|---|---|---|---|---|
| 54,414 | A | * | 5/1866 | Sanyster | 210/521 |
| 1,032,879 | A | * | 7/1912 | Carlton et al. | 210/532.1 |
| 2,467,547 | A | * | 4/1949 | Birnbaum | 210/532.1 |
| 4,326,952 | A | * | 4/1982 | Blake | 210/521 |
| 4,385,891 | A | * | 5/1983 | Ligotti | 433/92 |
| 4,761,235 | A | * | 8/1988 | Haentjens | 210/532.1 |
| 4,957,621 | A | * | 9/1990 | Rohloff | 210/521 |
| 5,114,578 | A | * | 5/1992 | Sundström | 210/521 |

* cited by examiner

Primary Examiner—Christopher Upton
(74) Attorney, Agent, or Firm—Barbara Rae-Venter; Rae-Venter Law Group (57) ABSTRACT

A device is provided for the filter and collection of one or more material. The device incorporates a manifold with an inlet conduit and an outlet conduit, with an adjustable control handle on the top of the manifold and a baffle plate in the inside of the manifold. The manifold is sealed to the top opening of a collection chamber. During procedures which require withdrawal of material not to be collected, the control handle and baffle plate are adjusted to a pass-through mode which connects a internal adjustable conduit, which transverses through the baffle plate, with the lumen of the inlet and outlet conduits to form a continuous lumen with which to withdraw material not to be collected through. During procedures which require the withdrawal of material to be collected, the control handle and baffle plate are adjusted to a solids mode which orients the baffle plate to face both the lumen of the inlet and outlet conduits. The material to be collected drawn by a vacuum is deflected by the baffle plate and fall by gravity into the collection chamber. The collection chamber is removable and can be covered by a lid. This device is useful for practitioners of dental procedures, jewelry manufacture or repair, scientific research, and other procedures that generate waste that require special disposal or material of value that can be recycled.

24 Claims, 4 Drawing Sheets

FILTER AND COLLECTION DEVICE FOR SEPARATING MATERIALS AND USE THEREOF

INTRODUCTION

This application is a Continuation-in-Part of prior application U.S. Ser. No. 09/176,812, filed Oct. 22, 1998 now U.S. Pat. No. 6,149,812, the disclosure of which is incorporated herein by reference.

FIELD OF THE INVENTION

This invention relates to a filter and collection device for the filtration, collection and isolation of materials and use thereof. The invention is exemplified by use of the device to separate heavy metals from non-heavy metal generated during dental procedures.

BACKGROUND

During procedures that generate waste where separation of different waste is desirable, procedures that generate waste and solids of value where separation of the solids of value and the waste is desirable, or procedures that generate small solids of value where the separation and collection of the small solid particles by material type is desirable, there is a lack of a device capable of filtering or separating material collected during or after these various procedures.

An example of one type of such procedures, where such a device would be of use is dental procedures. During dental procedures, typically the dental practitioner and dental assistant sit on adjustable stools on opposite sides of the reclined contour dental chair near the patient's head. The dentist prepares the patient's teeth for restoration with a high speed turbine handpiece (drill) and other instruments to remove decay and shape the tooth to be restored. During some parts of the procedure a water spray is used to wash the tooth and the operating field (washed field technique). Tooth structure particles and/or existing old defective silver-mercury amalgam or gold restorations are aspirated from the operating field of the oral cavity. This aspiration is done by the dental assistant using a vacuum tip attached to a conventional flexible vacuum tubing. The solids, water spray and oral fluids are deposited via the vacuum tubing into a perforated plastic screen located in the vacuum conduit line leading to the sewer line. However, solids of small size that escape the perforated plastic screen are deposited into the sewer line. The materials collected during oral surgery often include blood, gingivel tissue, suture clippings, pieces of bone, pus and other infection fluids. The materials collected during prophylaxis often include calculus and cleaning materials.

The dental filter currently in use suffers from many disadvantages and fails completely to accomplish the function of a dental filter:

(a) The particles of the silver-mercury amalgam, gold and tooth structure produced by the drilling procedure are reduced to a very small particle size. These small particles escape through the perforations of the plastic screen and are lost into the sewer system.

(b) Mercury, also a heavy metal, is a liquid at room temperature and in its free state is a very toxic substance. Therefore, if liquid mercury is accidentally spilled on operating surfaces or on the floor, it can be aspirated up by the vacuum tip. However, it easily escapes through the plastic screen perforations. The mercury then enters the sewer lines and ultimately into the environment.

(c) Another defective feature in the above described filter screen is that the water and oral fluids are aspirated together with the solid materials being removed from the oral cavity.

(d) The perforated screen type filter does not allow for the separation of different wastes during the dental procedure.

Other systems, while not using continuously running water as a vacuum source, nevertheless uses a centrally-located debris canister or variant thereof where the extracted debris is collected during operation. The disadvantage of such systems is that such a debris canister must be often and regularly emptied and, consequently the centrally located system must be shut down during this time. Such systems can present a significant problem when the canister must be emptied while the dentist is performing a dental procedure on a patient. Some of these systems incorporate mechanisms which are able to detect the moment of need for emptying the debris canister and are further capable of disposing of the contents therein. Such systems cannot separate heavy metals, including mercury, and other solids from non-heavy metal liquids.

Common to each of these dental vacuum systems is a problem associated with obtaining optimal dental waste mass flow rates while minimizing both negative vacuum pressures necessary for such flow rates and facilities space needed for locating the vacuum canisters. The optimal dental waste mass flow rate is approximately 5 cubic feet per minute. Heretofore, such a mass flow rate is obtainable only when 40–55 gallon debris canisters and their associated high required negative vacuum pressures are used in conjunction therewith. Additionally, installation or removal of these dental vacuum systems require considerable plumbing or property improvements to access the required water, vacuum lines, and electricity. In such a case, the inconvenience and expense incurred by the dental practitioner can be considerable.

Another example of procedures that such a filter and collection device would be of use is jewelry manufacture and repair, and lapidary procedures. There is a lack of a device that can separate and collect the different precious material cast as carvings, trimmings, filings, shavings or the like. The common practice is to use a different holding tray for each precious material to be worked on. However, this system has the disadvantage of requiring further consolidation of the carvings, trimmings, filings, shavings or the like from each tray and the storage of the various trays is space consuming, tedious, and inefficient.

Another example of procedures that such a filter and collection device would be of use is in scientific research procedures that involve the use of biological hazardous waste, radioactive material, carcinogens, mutagens or other toxic or noxious materials that are spilled or to be disposed of as waste. There is lack of a device that can separate and collect the toxic or noxious materials. The common practice is to put these materials into a plastic bag by hand with gloves as protection, and to dispose of the plastic bags and gloves. When there is an accidental spill of liquid waste, then the liquid is first absorbed by absorbent material, such as paper towels. However, this system has the disadvantage of proximity of the hand to the material being disposed of, the generation of more tainted waste, including the absorbent material, gloves, and plastic bags.

It therefore is of interest to develop a device capable of separating solid material from liquid material, one solid material from another solid material, and one liquid material from another liquid material. This device would be capable of being easily adapted to current vacuum systems, inexpensive to manufacture, able to salvage materials of value, and able separately collected waste materials requiring special disposal, such as mercury, biological hazardous waste, radioactive waste, carcinogens, mutagens, and other toxic or noxious waste.

RELEVANT LITERATURE

U.S. Pat. No. 4,326,952 (1982) to Blake discloses an apparatus for recovering precious metal particles from a liquid mixture environment which utilizes a plurality of baffled compartments successively arranged in a sealed chamber.

U.S. Pat. No. 4,385,891 (1983) to Ligotti discloses a dental apparatus for preventing loss of precious metal particles from a mixture drawn from the mouth of a dental patient using a perforated baffle.

U.S. Pat. No. 4,564,374 (1986) to Hofmann discloses a device for incorporation in dental suction apparatuses for separation of liquid and solid components.

U.S. Pat. No. 4,761,235 (1988) to Haentjens discloses a waste collection device for accumulating solid waste downstream of a kitchen garbage grinder, which includes a separator for settling solid material from waste water and a removable waste accumulating container into which household garbage is collected.

U.S. Pat. No. 4,957,621 (1990) to Rohloff discloses a water jet cutting system, which uses a baffle plate to remove abrasives from the liquid before the liquid is passed through it.

U.S. Pat. No. 5,114,578 (1992) to Sundstrom discloses a settling apparatus for the separation of amalgam from waste water in a dental procedure, which includes an inclined passage through which water is caused to flow from below and upwards while depositing amalgam.

U.S. Pat. No. 5,741,397 (1998) to Kraver discloses an apparatus for processing combined liquid and solid dental waste from a patient's mouth such that the solid waste is separated from the liquid waste.

U.S. Pat. No. 5,797,742 (1998) to Fraker discloses an amalgam solids collecting apparatus of the type for collecting an accumulation of a generally separable mixture of solids and liquids, including amalgam solids, and separating the solids from the liquids.

U.S. Pat. No. 5,967,780 (1999) to Morrissey discloses a vacuum receptacle method for accumulating, holding and disposing of liquids and certain solids that are evacuated from the mouths of dental patients by a suction tube during dental procedures, wherein a baffle is provided to impact and decelerate dental debris as it enters the receptacle.

SUMMARY OF THE INVENTION

Figure 3:
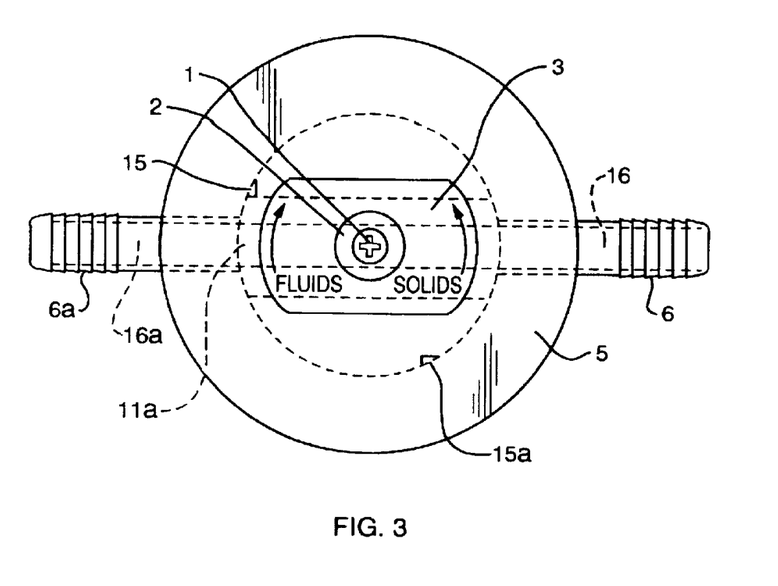
FIG. 3 is a top view, looking down on the top of the environmental filter with the control handle in pass-through mode.

The invention is a device that can separate and collect materials by using an air flow created by a conventional vacuum system, a manifold, a collection chamber, an adjustable baffle plate, and the force of gravity. The invention allows for the separation of any material (collect mode) from another material (pass-through mode). The device is switched from the collect mode to the pass-through mode by simply adjusting the position of the adjustable baffle plate. In the collect mode, any material drawn in by vacuum strikes the baffle plate, and by the effect of gravity falls into the collection chamber. When the chamber is sufficiently filled, the chamber is unscrewed from the manifold and a lid is screwed onto the chamber. This seals the chamber for storage of the collected material. A new collection chamber is then screwed into its place in the manifold. In the pass-through mode (FIGS. 3, 3A), material not desired to be collected bypasses the face of the baffle plate and the collection chamber. The invention encompasses the use of the device to separate one material from another material. The invention also encompasses the method of separating and collecting one material from another material by aspirating one material so that it bypasses the collection chamber, adjusting the position of the baffle plate, aspirating another material so that it is deflected by the baffle plate into the collection chamber. This device finds use in the separation of one or more precious and/or toxic substance for jewelers, goldsmith, gemologists, and like professionals.

BRIEF DESCRIPTION OF THE DRAWINGS

FIG. 3B shows the underside of the control handle.

DESCRIPTION OF THE SPECIFIC EMBODIMENTS

The invention is a device that can separate and collect materials by using an air flow created by a conventional vacuum system, a manifold, a collection chamber, an adjustable baffle plate, and the force of gravity. The invention allows for the separation of one material (collect mode) from another material (pass-through mode). The device is switched from the collect mode to the pass-through mode by simply adjusting the position of the adjustable baffle plate. This adjustment can be accomplished by manually turning a control handle or by connecting the baffle plate to a motor which is electrically linked to a switch. In the collect mode, any material drawn in by vacuum strikes the baffle plate, and by the effect of gravity falls into the collection chamber. When the chamber is sufficiently filled, the chamber is unscrewed from the manifold and a lid is screwed onto the chamber. This seals the chamber for storage of the collected material. A new collection chamber is then screwed into its place in the manifold. In the pass-through mode (FIGS. 3, 3A), material not desired to be collected bypasses the face of the baffle plate and the collection chamber. The device can be fitted with a vacuum safety float assembly so that the user of the device can be warned in advance in case the collection chamber accumulates too much material in order for the user to empty the collection chamber or to replace it with an empty collection chamber. In addition, the vacuum safety float can be linked to a switch which shuts down the vacuum system when the accumulation reaches a critical level, particularly if collecting only liquids in the collection chamber. The collection chamber can also be fitted with a smaller container inside the collection chamber. The base or the smaller container can be fitted with a netting, sieve, mesh or like base with perforations to allow liquid or small solid material to pass through and be deposited at the bottom of the collection chamber, while larger solid material is collected in the smaller container. The invention encompasses the use of the device to separate one material from another material. The invention also encompasses the method of separating and collecting one material from another material by aspirating one material so that it bypasses the collection chamber, adjusting the position of the baffle plate, aspirating another material so that it is deflected by the baffle plate into the collection chamber. All parts of this invention can be composed of plastic which will not allow for corrosion of the parts. The invention can be easily manufactured by any plastics company which manufactures plastic parts or plastic implements. In addition, parts of the invention can be composed of metal, glass, ceramics, rubber or other like durable material which can withstand the low pressure generated by a vacuum system. The collection chamber can be manufactured using a transparent or translucent material so that the level of material collected in it can be determined by the user with a simple visual inspection. The collection chamber can also be marked, either on the inside or in the side, with markings to indicate graduations of volume or other units of measurement.

The advantage of the invention is that one material can be separated from another material by aspirating the material to be collected when the device is in the collect mode, and aspirating the material not be collected in the pass-through mode. The use of the collect mode and the pass-through mode allows a user to determine which materials to be collected and which can be immediately disposed of by passing through the device directly to the sewers. The ability to filter and collect only the material desired to be collected helps to eliminate or greatly reduce the amount of potential contaminants entering the sewer system, and also helps to collect material of value so that these materials can be salvaged and recycled instead of being lost as waste or lost into the sewer system. Since waste that can contaminate the environment can be collected to avoid its disposal into the sewer lines, no separate waste disposal system, which collects all waste generated, is required. An another advantage is that since the collection chamber is removable means that different materials to be collected can be collected in different collection chambers, so that waste requiring special disposal is not mixed with materials of value that are to be recycled. An another advantage is that the device can be attached to any existing vacuum system without the need to renovate the vacuum or plumbing system. An another advantage is when many different materials of value are collected, the collection of these materials in different collection chambers can allow for convenient and efficient storage. An another advantage is that liquid waste can be directly aspirated into the collection chamber so as to avoid or reduce the need for absorbent material and thus reduce waste. The device is simple and inexpensive to manufacture.

Figure 1:
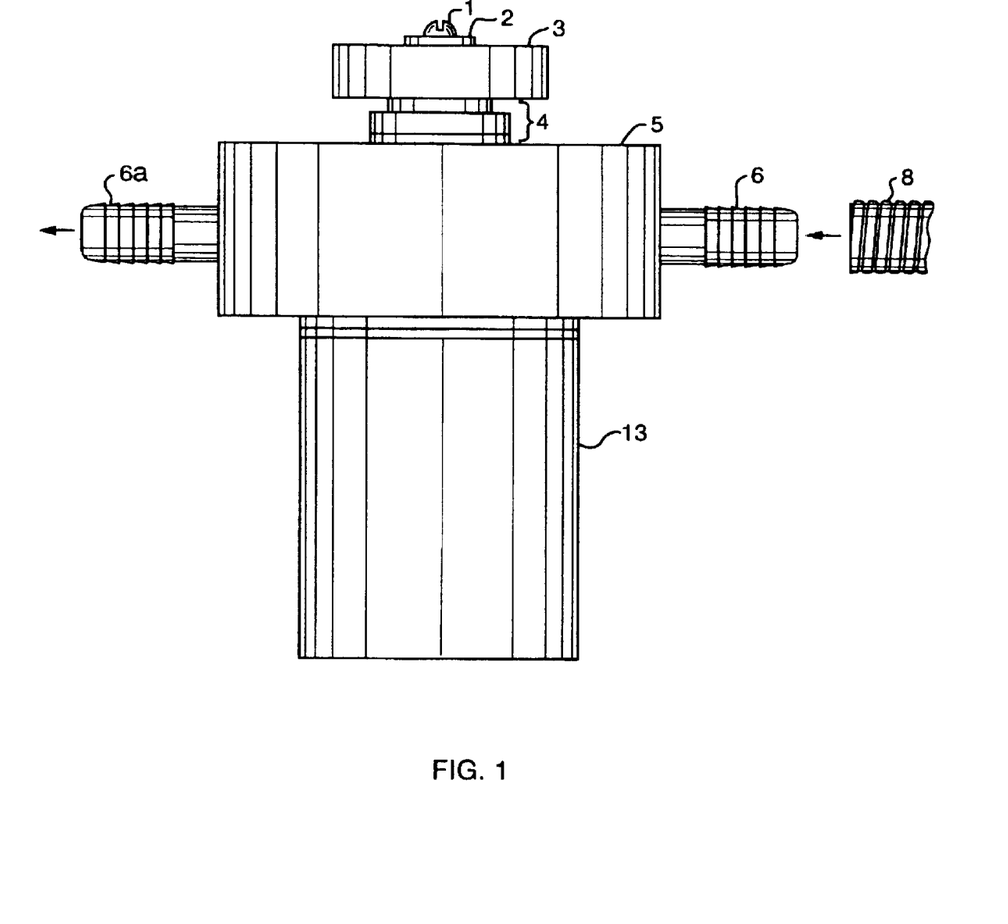
FIG. 1 is a side view of the environmental filter.
Figure 2:
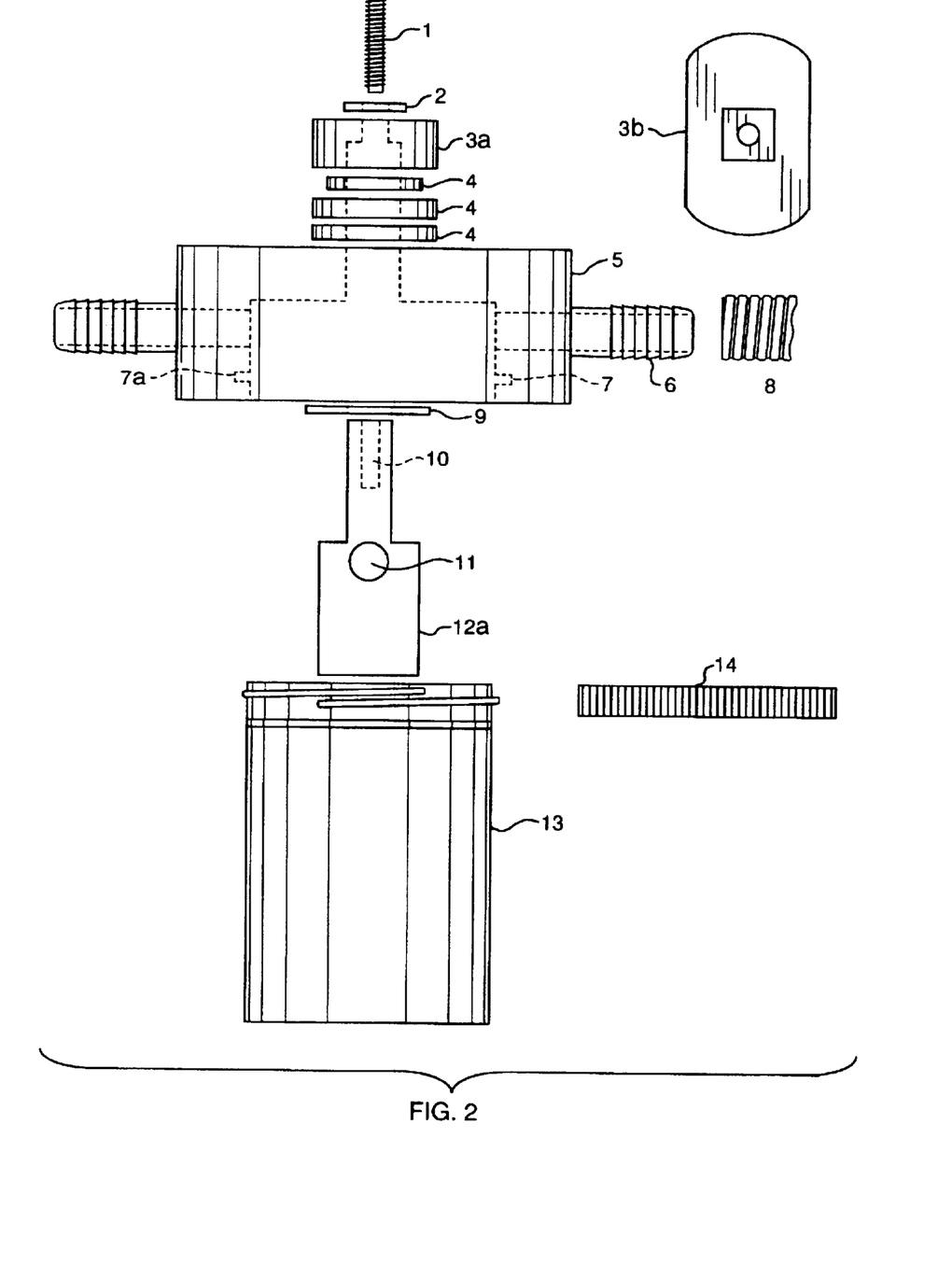
FIG. 2 is an explosion side view of all the parts of the environmental filter.
Figure 3A:
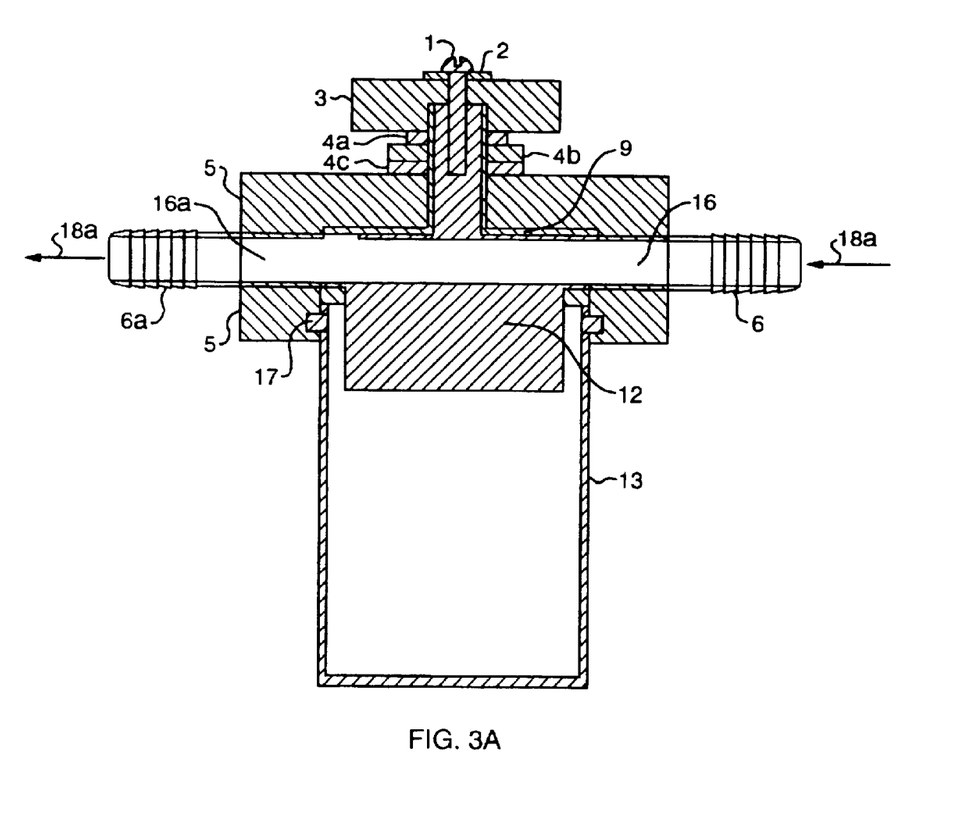
FIG. 3A is a side sectional of the environmental filter view in the pass-through mode.
Figure 4:
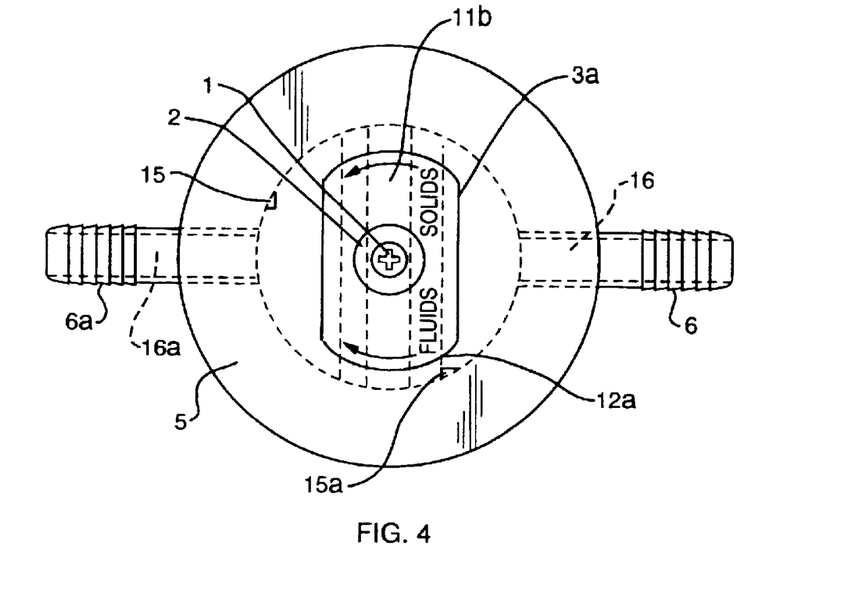
FIG. 4 is a top view, looking down on the top of the environmental filter with the control handle in the collect mode.
Figure 4A:
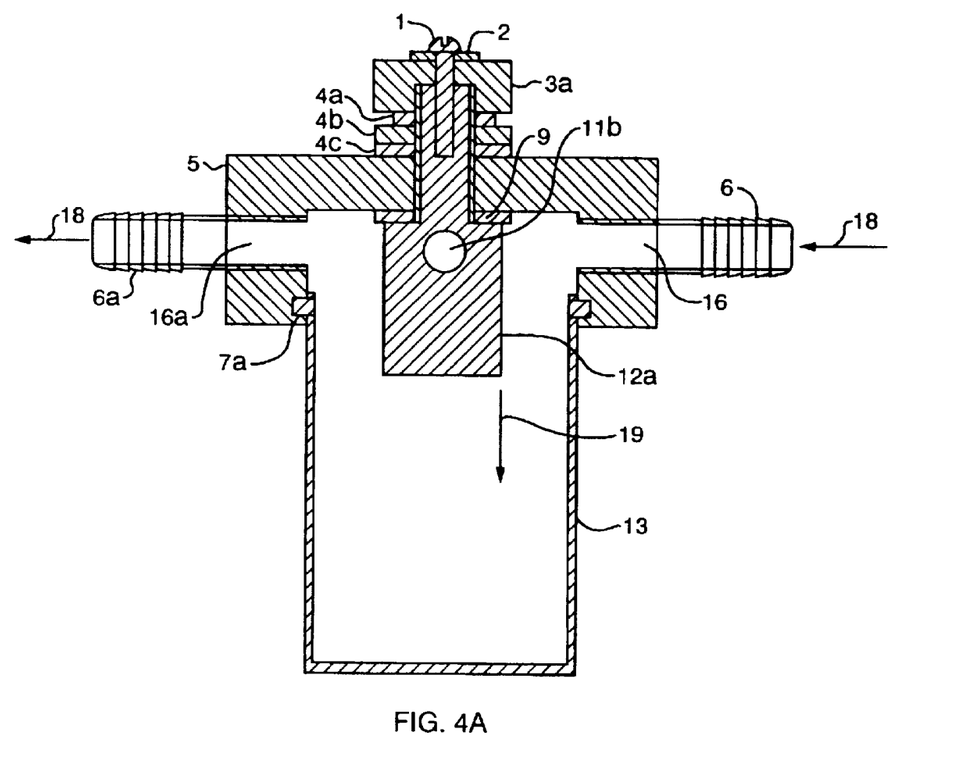
FIG. 4A is a sectional view of the environmental filter in the collect mode.

An embodiment of the invention is shown in FIGS. 1 and 2. A screw 1 holds the control handle 3 in place which screws into the extended neck threads 10 of the conduit/baffle partition. There is a plastic washer 2 between the screw 1 and the control handle 3. The control handle 3 can be positioned in the pass-through mode 3 or the collect mode 3A. 3B shows the underside of the control handle. Washers 4A, 4B, 4C between the control handle 3 and the top of the manifold 5 elevate the control handle 3 for turning convenience and to reduce friction when turning the control handle 3. The manifold 5 provides outlets through which vacuum air, fluids and solid materials are distributed. The manifold 5 coordinates and holds together the principal parts of the invention. These are the entry external conduit 6 and exit external conduit 6A, to which conventional vacuum tubing 8 is fastened. The entry external conduit 6 and exit external conduit 6A direct the directions of the incoming air 18 and the outgoing air 18A. Female threads 7, 7A in the manifold 5 join with the male threads 17 of the collection chamber 13. The washer 9 between the manifold 5 and the baffle plate/internal conduit portion assist in the free turning of the internal adjustable conduit (lumen) 11 and the baffle plate 12. The female threads 10 in the neck (top) portion of the internal conduit/baffle plate receive the screw 1. In the pass-through mode, the internal adjustable conduit (lumen) 11A located in the baffle plate 12 is turned 90° clockwise from the collect mode orientation. In the pass-through mode, FIGS. 3, 3A the adjustable internal conduit (lumen) 11A forms a continuous lumen with the entry internal conduit (lumen) 16 and the exit internal conduit (lumen) 16A, located in the manifold 5 portion. In the collect mode, FIG. 4, 4A the internal adjustable conduit (lumen) 11B located in the baffle plate 12A is turned 90° counter-clockwise from the pass-through mode orientation. The baffle plate 12A, when in the collect mode orientation, deflects materials to be collected into collection chamber 13. Lid 14 is for covering the collection chamber 13. A stop 15 is located inside the manifold 5 FIGS. 3, 3A to control the orientation of the internal adjustable conduit 11A for the pass-through mode. A stop 15A FIG. 4 is located inside the manifold 5 to control the orientation of the adjustable conduit-baffle plate 12A for the collection mode. The entry internal conduit (lumen) 16 forms a continuous lumen with the entry external conduit 6. The exit internal conduit (lumen) 16A forms a continuous lumen with the exit external conduit 6A. Arrow 18 FIG. 4A depicts the direction of vacuum flow during the collect mode. Arrow 18A FIG. 3A depicts the direction of vacuum air flow and flow of material not desired to be collected during the pass-through mode. The vertical arrow 19 depicts the direction of the materials to be collected falling toward the bottom of the collection chamber 13 due to the collision of the materials with the baffle plate 12A and due to the effect of gravity on the materials.

Tubing 8 FIG. 2, such as conventional plastic tubing, is fastened to the entry external conduit 6 and exit external conduit 6A, which are located entering and exiting each side of a manifold 5. The exit external conduit 6A is connected to a conventional vacuum source via conventional vacuum tubing 8 FIG. 2 and exits into the sewage system.

The control handle 3 is turned 90° to the pass-through mode. In the pass-through mode no material is collected. In the pass-through mode (see FIGS. 3 and 3A), material not desired to be collected move by conventional vacuum pressure through the tubing 8, through the entry external conduit 6, through the entry internal conduit 16, through the adjustable internal conduit 11A, through the exit internal conduit 16A, through the exit external conduit 6A, and exiting through conventional vacuum tubing 8. Thus, during the pass-through mode, material not desired to be collected totally bypasses the collection chamber 13.

The collect mode is used during the collection phase of material desired to be collected. The control handle 3A is turned 90° to the collect mode. In the collect mode (see FIGS. 4 and 4A), material to be collected is drawn through the tubing 8, through the entry external conduit 6, and through the entry internal conduit 16. The material to be collected then strike the baffle plate 12A from where the material drop in the direction indicated by the arrow 19, due to gravity, into the collection chamber 13. The invention can be used in any procedure where one material is to be separated from another materials.

In another embodiment the control handle 3 can be turned to a third position, whereby the position of the baffle plate will seal or block the lumen of inlet conduit 16 and the outlet conduit 16A. This stops all aspiration to the device.

Optionally, a safety valve can be attached to the manifold 5 or the collection chamber 13 or another suitable part of the filter so that the low pressure applied can be shut off by opening the inside of the filter to the atmosphere. However, simply shutting off the vacuum air applied to the filter. The optional safety valve can be designed to be manually operated.

When the collection chamber 13 has been sufficiently filled with material, the jar is unscrewed form the manifold 5 and sealed with a lid 14 for storage or transport to another location. Another collection chamber 13, that is empty, is then screwed into place in manifold 5. The level of material collected in the collection chamber 13 can be determined a variety of means. The collection chamber can be wholly or partially constructed of a substance that is transparent or translucent so that the level of material collected can be determined by visual inspection. It is preferable that the collection chamber be made of material at least as strong as the vacuum pressure tubing so that the collection chamber does not collapse in the event that the aspirating tip is closed while the vacuum source is still on.

The invention can be practiced by dental practitioners performing dental surgery, oral surgery, prophylactic procedures or other dental procedures. Conventional plastic vacuum tubing 8 is fastened to entry external conduit 6 and exit external conduit 6A, which are located entering and exiting each side of a manifold 5. The exit external conduit 6A is connected to a conventional vacuum source via conventional vacuum tubing 8 and exits into the sewage system. In one embodiment the assembled environmental filter can be fastened to a conventional dental light post using a conventional plastic strap. The operation of the environmental filter can be done by the chairside dental assistant while assisting the dental practitioner in the dental procedures. The control handle 3 is turned 90° to the pass-through mode. In the pass-through mode no heavy metal, mercury or other solid material is being collected. The pass-through mode allows for the aspiration of water spray used during drilling procedures on teeth (washed field technique) or other dental or oral procedures and the aspiration of oral fluids such as blood, pus, or saliva or other fluids during oral surgery procedures. The term "non-heavy metal liquids" is intended to mean all liquids except mercury. In the pass-through mode (see FIGS. 3 and 3A), non-heavy metal liquids move by conventional vacuum pressure through the dental assistant's conventional aspirating tip, conventional vacuum tubing 8, through the entry external conduit 6, through the entry internal conduit 16, through the adjustable internal conduit 11A, through the exit internal conduit 16A, through the exit external conduit 6A, and exiting through conventional vacuum tubing 8, finally emptying into the sewer line or a collection container for non-heavy metal liquids waste. Thus, during the pass-through mode, air and non-heavy metal liquids drawn by the vacuum bypasses the collection chamber 13, and deposits the fluids directly into the sewage line.

The collect mode is used during the collection phase of the heavy metals, mercury, and other solid materials. The control handle 3A is turned 90° to the solids mode. The solid materials are old, defective silver-mercury amalgam or gold restorations that are being removed during the preparation of teeth for new restorations. The solid materials also include the silver-mercury amalgam carvings resulting from shaping new silver-mercury amalgam fillings. In the collect mode (see FIGS. 4 and 4A), as the dentist carves the anatomy of the still malleable silver-mercury amalgam, the dental assistant aspirates amalgam carvings (i.e., the heavy metals) by conventional vacuum pressure through the dental assistant's conventional aspirating tip, conventional vacuum tubing 8, through the entry external conduit 6, and through the entry internal conduit 16. The heavy metals then strike the baffle plate 12A from where the heavy metal, mercury, and other solid material drop in the direction indicated by the arrow 19, due to gravity, into the collection chamber 13. Any excess heavy metal restorative materials, or accidentally spilled mercury on operating surfaces or the floor, can be aspirated into the heavy metals collection chamber 13 in the same manner. The invention can be used in any procedure, dental or otherwise, where solid materials and liquid materials need to be separated. Thus, these heavy metal materials can be collected for the purpose of recycling finite heavy metals. Mercury, which is very toxic in its free state, is prevented from entering and contaminating the environment. When the collection chamber 13 has been sufficiently filled with heavy metals, the jar is unscrewed from the manifold 5 and sealed with a lid 14 for storage and recycling of the heavy metals. An empty heavy metals collection chamber 13 is then screwed into place in manifold 5. The level of solids or mercury collected in the collection chamber 13 can be determined a variety of means. The collection chamber can be wholly or partially constructed of material that is transparent or translucent so that the level of solids or mercury collected can be determined by visual inspection.

In addition to the use of a control handle to adjust the baffle plate, the baffle plate optionally can be connected to a motor which is electrically linked to a switch placed near where material is drawn in by aspiration by the dental practitioner or dental assistant during dental procedures, or a switch on a dental instrument (such as the high speed turbine hand drill), or any other convenient location, so that the environmental filter can be switched from the pass-through mode to the collection mode or vice versa conveniently by the dental practitioner or dental assistant during a dental procedure without needing to manually adjust the baffle plate with the control handle.

Where the collection chamber is used to collect liquids, particularly toxic waste liquids such as mercury, for capture and disposal, the device can be fitted with a vacuum safety float assembly so that the dental practitioner can be warned in advance in case the collection chamber accumulates too much material so that such accumulated material is at risk of being pulled into the vacuum source and ultimately into the sewer system. The vacuum safety float assembly can provide advance warning to the dental practitioner before the risk of over accumulation in the collection chamber is too great in order that the collection chamber can be replaced or emptied. In addition, or the alternative, the vacuum safety float can shut down the system when the accumulation reaches a critical level.

In certain instances solids, such as gold carvings, may be suspended in liquids and it is difficult to avoid aspirating the solids without also aspirating the liquids. In order to effectively separate such solids from such liquids, the collection chamber optionally can be further modified by fitting a smaller container within the collection chamber whereby the base of the smaller container is a netting, sieve, mesh or the like, or contains perforations to allow the liquids to remain in the collection chamber when the smaller container is removed from the collection chamber.

All parts of this invention can be composed of plastic which avoids corrosion of the parts. The invention can be easily manufactured by any plastics company which manufactures plastic parts or plastic implements. In addition, parts of the invention can be composed of metal, glass, ceramics, rubber or other like durable material which do not react with the materials into which they will come in contact.

The invention keeps heavy metals collected in a dry state. This is important for storage while awaiting to be sent out for recycling of the recovered heavy metals. The invention captures mercury for recycling and prevents the free mercury, which is toxic, from contaminating the environment. The invention can be easily disassembled for cleaning purposes by the dental staff members.

Another advantage of the invention is that it can be easily incorporated into the vacuum system of any dental clinic without need for renovating the vacuum or plumbing system: resulting in substantial savings in both cost and time.

The invention can also be practiced by practitioners of other professions in which solids and liquids need to be separated or certain solids need to be separated from other solids. The invention can also be used in tandem when more than one solid or liquid needs to be separated from one another. For example, the practitioner of jewelry manufacturer when working with different precious metals, such as platinum, gold, white gold, red gold, silver and other metals or alloys of value, different precious minerals, such as diamond, emerald, ruby, sapphire, opal, quartz, mother-of-pearl, and other minerals of value, and other precious materials, can use the invention to separate and collect carvings, shavings, facetings, and the like, of these precious materials. A separate collection chamber can be used for each different material collected, so that each time a different material is to be collected, the corresponding collection chamber for that material is attached to the manifold. Alternatively, a plurality of the devices of the invention can be linked in series or parallel, so that when one material is to be collected, the control handle corresponding to that collection chamber is switched to the collect mode and all other filters are switched to the pass-through mode. Any material aspirated will then be deposited only into the collection chamber of the separator which is switched to the collect mode.

The invention can also be practiced by researchers when certain solids or liquids need to be separated from other solids or liquids because the former require special treatment and/or disposal. For example, the disposal of biological hazardous waste, such as infectious fluids, pathogenic bacteria, human viruses and the like, require special treatment prior to disposal. For such uses, the collection chamber, prior to use, is partially filled with hypochlorate, a bleaching agent, a strong acid or any other disinfecting or antiseptic agent appropriate for treating the waste material. In another use, the solid or liquid waste can be separated from other material for disposal. For example, radioactive material or reagents, carcinogens, mutagens and other toxic or noxious material, can be collected separately and disposed of as appropriate for the nature of the waste. For example, due to the scarcity of landfills dedicated to storing radioactive waste, the volume of radioactive waste to be disposed should be minimized.

The examples in this application are offered by way of illustration and not by way of limitation.

All publications and parent applications mentioned in this specification are indicative of the level of skill in the art to which this invention pertains. All publications and parent applications are herein incorporated by reference to the same extent as if each individual publication or patent application was specifically and individually indicated to be incorporated by reference.

The invention now having been fully described, it will be apparent to one ordinarily skilled in the art that many changes and modifications can be made thereto without departing from the spirit or scope of the appended claims.

What is claimed is:

1. A separator for separating a first composition from a second composition by gravity comprising:
    a manifold having a first conduit and a second conduit;
    a baffle plate between a first conduit and a second conduit, said baffle plate having an internal conduit extending through said baffle plate; and
    a collection chamber below said manifold; wherein said baffle plate being adjustable between at least two positions; wherein in a first position said baffle plate is interposed between said first conduit and said second conduit, wherein said baffle plate forms means for deflecting said first composition into said collection chamber; and in a second position, wherein said internal conduit is in communication with said first conduit and second conduit, wherein said internal conduit forms means to bypass said collection chamber.

2. The separator according to claim 1 wherein said baffle plate is adjustable to a third position wherein said first conduit and said second conduit are both totally blocked.

3. The separator according to claim 1, wherein said collection chamber contains a means to detect the level of said first composition in said collection chamber when it reaches a certain level in said collection chamber and this information is communicated to the outside of the collection chamber.

4. The separator according to claim 1, wherein said first composition comprises at least one solid material and at least one liquid material, and said collection chamber comprises an upper collection chamber and a lower collection chamber, wherein a means to separate said solid material and said liquid material is interposed between said upper collection chamber and said lower collection chamber.

5. The separator according to claim 4, wherein said means to separate said solid material and said liquid material is a filter.

6. The separator according to claim 1 wherein said collection chamber is wholly or partially composed of a transparent or translucent material whereby the accumulation of first composition in said collection chamber can be visually detected.

7. The separator according to claim 1, wherein said baffle plate is adjustable using a control handle.

8. A method for separating a first composition from a second composition, said method comprising:
    (a) aspirating said second composition through a manifold so that said second composition bypasses a collection chamber,
    (b) adjusting orientation of a baffle plate attached to said manifold,
    (c) aspirating said first composition so that said first composition is deposited in said collection chamber, and
    (d) performing step (b) in order to switch between steps (a) and (c)
        whereby said first composition is separated from said second composition.

9. The method according to claim 8 wherein said first composition is a composition of value or a composition requiring special disposal.

10. The method according to claim 9 wherein said composition of value comprises at least one selected from the group consisting of silver-mercury amalgam, platinum, gold, white gold, red gold, silver, diamond, emerald, ruby, sapphire, opal, quartz, and mother-of-pearl.

11. The method according to claim 9 wherein said composition requiring special disposal comprises at least one selected from the group consisting of mercury, biological hazardous waste, infectious fluids, pathogenic bacteria, human viruses, radioactive material or reagents, carcinogens, and mutagens.

12. A method for separating a first composition from a second composition, said method comprising:

adjusting the position of a baffle plate so that one position causes aspirated said second composition to bypass a collection chamber, while another position causes said first composition to be deposited in said collection chamber, whereby said first composition is separated from said second composition.

13. The method of claim 12, wherein said adjusting is turning said baffle plate 90° clockwise or counter-clockwise.

14. The method of claim 13, wherein said turning is manually turning a control handle that is attached to said baffle plate.

15. The method according to claim 12 wherein said first composition is a composition of value or a composition requiring special disposal.

16. The method according to claim 15 wherein said composition of value comprises at least one selected from the group consisting of silver-mercury amalgam, platinum, gold, white gold, red gold, silver, diamond, emerald, ruby, sapphire, opal, quartz, and mother-of-pearl.

17. The method according to claim 15 wherein said composition requiring special disposal comprises at least one selected from the group consisting of mercury, biological hazardous waste, infectious fluids, pathogenic bacteria, human viruses, radioactive material or reagents, carcinogens, and mutagens.

18. A method for separating a first composition from a second composition, said method comprising:

(a) introducing a barrier to deflect said first composition into a collection chamber, and (b) removing said barrier to allow said second composition to bypass said collection chamber, wherein said barrier is adjustable so that steps (a) and (b) are interchangeable.

19. The method according to claim 18 wherein said first composition is a composition of value or a composition requiring special disposal.

20. The method according to claim 19 wherein said composition of value comprises at least one selected from the group consisting of silver-mercury amalgam, platinum, gold, white gold, red gold, silver, diamond, emerald, ruby, sapphire, opal, quartz, and mother-of-pearl.

21. The method according to claim 19 wherein said composition requiring special disposal comprises at least one selected from the group consisting of mercury, biological hazardous waste, infectious fluids, pathogenic bacteria, human viruses, radioactive material or reagents, carcinogens, and mutagens.

22. A separator for separating a first composition from a second composition by gravity comprising:

a manifold having a first conduit and a second conduit;

a baffle plate between a first conduit and a second conduit, said baffle plate having an internal conduit extending through said baffle plate; and a collection chamber below said manifold, wherein said baffle plate being adjustable between at least two positions; wherein in a first position said baffle plate is interposed between said first conduit and said second conduit, wherein said baffle plate forms means for deflecting said first composition into said collection chamber, and in a second position, wherein said internal conduit is in communication with said first conduit and said second conduit, wherein said internal conduit forms means to bypass said collection chamber;

whereby collection of said first composition in said collection chamber is a collection of a composition of value or a composition requiring special disposal.

23. A separator for separating a first composition from a second composition by gravity comprising:

a manifold having a first conduit and a second conduit;

a baffle plate between a first conduit and a second conduit, said baffle plate having an internal conduit extending through said baffle plate; and a collection chamber below said manifold, wherein said baffle plate being adjustable between at least two positions; wherein in a first position said baffle plate is interposed between said first conduit and said second conduit, wherein said baffle plate forms means for deflecting said first composition into said collection chamber, and in a second position, wherein said internal conduit is in communication with said first conduit and said second conduit, wherein said internal conduit forms means to bypass said collection chamber;

whereby collection of said first composition in said collection chamber is a composition of value that comprises at least one selected from the group consisting of silver-mercury amalgam, platinum, gold, white gold, red gold, silver, diamond, emerald, ruby, sapphire, opal, quartz, and mother-of-pearl.

24. A separator for separating a first composition from a second composition by gravity comprising:

a manifold having a first conduit and a second conduit;

a baffle plate between a first conduit and a second conduit, said baffle plate having an internal conduit extending through said baffle plate; and a collection chamber below said manifold, wherein said baffle plate being adjustable between at least two positions; wherein in a first position said baffle plate is interposed between said first conduit and said second conduit, wherein said baffle plate forms means for deflecting said first composition into said collection chamber, and in a second position, wherein said internal conduit is in communication with said first conduit and said second conduit, wherein said internal conduit forms means to bypass said collection chamber;

whereby collection of said first composition in said collection chamber is a composition requiring special disposal that comprises at least one selected from the group consisting of mercury, biological hazardous waste, infectious fluids, pathogenic bacteria, human viruses, radioactive material or reagents, carcinogens, and mutagens.

* * * * *

UNITED STATES PATENT AND TRADEMARK OFFICE
CERTIFICATE OF CORRECTION

PATENT NO.     : 6,592,769 B1
DATED          : July 15, 2003
INVENTOR(S)    : Erickson et al.

It is certified that error appears in the above-identified patent and that said Letters Patent is hereby corrected as shown below:

Title page,
Item [57], ABSTRACT,
Line 2, "material" should read -- materials --;
Line 3, after "conduit,", delete "with";
Line 4, "manifold and" should read -- manifold, and --;
Line 9, after "which connects", "a" should read -- an --;
Line 12, "through" should read -- therethrough --;
Line 17, after "collected", insert -- is --;
Line 17, after "a vacuum", "is" should read -- and --;
Line 18, "plate and" should read -- plate, and --; and
Line 18, "fall" should read -- falls --.

Column 2,
Line 9, "uses" should read -- use --.

Column 3,
Line 3, after "and able" insert -- to -- ; also on line 3, "collected" should read -- collect --.

Column 5,
Lines 40, 45, 47 and 51, "An another" should read -- Another --.

Column 7,
Line 13, "form" should read -- from --.
Line 17, after "determined", insert -- by --;
Line 59, "bypasses" should read -- bypass --;
Lines 59-60, "deposits the fluids" should read -- are deposited --.

UNITED STATES PATENT AND TRADEMARK OFFICE
CERTIFICATE OF CORRECTION

PATENT NO. : 6,592,769 B1
DATED : July 15, 2003
INVENTOR(S) : Erickson et al.

It is certified that error appears in the above-identified patent and that said Letters Patent is hereby corrected as shown below:

<u>Column 10,</u>
Line 11, after "between", "a" should read -- said--;
Line 11, after "conduit and", "a" should read -- said --.

Signed and Sealed this

Thirtieth Day of March, 2004

JON W. DUDAS
*Acting Director of the United States Patent and Trademark Office*